United States Patent [19]
Wernicke et al.

[11] Patent Number: 5,231,988
[45] Date of Patent: Aug. 3, 1993

[54] TREATMENT OF ENDOCRINE DISORDERS BY NERVE STIMULATION

[75] Inventors: Joachim F. Wernicke, League City; Reese S. Terry, Jr., Houston, both of Tex.

[73] Assignee: Cyberonics, Inc., Webster, Tex.

[21] Appl. No.: 743,155

[22] Filed: Aug. 9, 1991

[51] Int. Cl.⁵ ............................................. A61N 1/36
[52] U.S. Cl. ..................................... 128/421; 128/637
[58] Field of Search ................. 128/421, 637, 419 R, 128/419 C

[56] References Cited

U.S. PATENT DOCUMENTS

| | | | |
|---|---|---|---|
| 4,761,287 | 8/1988 | Geho | 514/866 |
| 4,865,048 | 9/1989 | Eckerson | 128/791 |
| 4,867,164 | 9/1989 | Zabara | 128/421 |

Primary Examiner—Kyle L. Howell
Assistant Examiner—Kennedy J. Schaetzle

[57] ABSTRACT

Method and apparatus are described for treating and controlling diabetes and other systemic pancreatic endocrine disorders attributable to abnormal levels of secretion of endogenous insulin. An electrical stimulator implanted into or worn external to the patient's body is adapted, when activated, to generate a programmable electrical waveform for application to electrodes implanted on the vagus nerve of the patient. The electrical waveform is programmed using parameter values selected to stimulate or inhibit the vagus nerve to modulate the electrical activity thereof to increase or decrease secretion of natural insulin by the patient's pancreas. The stimulator is selectively activated manually by the patient in response to direct measurement of blood glucose or symptoms, or is activated automatically by programming the activation to occur at predetermined times and for predetermined intervals during the circadian cycle of the patient. Alternatively, the automatic activation is achieved using an implanted sensor to detect the blood glucose concentration, and is triggered when the patient's blood glucose concentration exceeds or falls below a predetermined level depending on whether diabetes or hypoglycemia is being treated.

22 Claims, 2 Drawing Sheets

TREATMENT OF ENDOCRINE DISORDERS BY NERVE STIMULATION

BACKGROUND OF THE INVENTION

The present invention relates generally to methods and apparatus for treating or controlling medical, psychiatric or neurological disorders by application of modulating electrical signals to a selected nerve or nerves of the patient, and more particularly to techniques for treating patients with diabetes and other systemic pancreatic disorders by application of such signals to a cranial nerve, using an implantable neurostimulating device, and specifically, by selective modulation of vagus nerve electrical activity.

Systemic disorders share a common pattern of multifocal or diffuse involvement of the nervous system including the cerebral hemispheres, the brain stem, the cerebellum, the spinal cord, the peripheral nerves and muscle. Among such disorders which are attributable to organ failure or disordered function, in contrast to those due to a specific pathological entity or pathological process, are the endocrine disorders. Disorders of the endocrine glands and neurological abnormalities may be linked in various clinical syndromes. Among the endocrine disorders are the pancreatic disorders of hypoglycemia and diabetes mellitus. Hypoglycemia is generally defined as a blood glucose concentration of less than 40 milligrams (mg) per 100 milliliters (ml) associated with suggestive signs and symptoms which vary with age and rapidity of onset of the hypoglycemia. The most common situation in which hypoglycemia occurs in humans is in the diabetic who is either taking insulin or a long-acting hypoglycemic agent. Typically, the diabetic is able to recognize the symptoms of hypoglycemia and to take the necessary action in avoidance (e.g., reduced dosage of insulin).

Diabetes is a condition characterized by excessive excretion of urine, either as a result of a deficiency of antidiuretic hormone (diabetes insipidus) or as a result of hyperglycemia, an abnormally high level of glucose in the blood (diabetes mellitus). The present invention is concerned primarily with treatment of diabetes mellitus, which is a complex disorder of carbohydrate, fat and protein metabolism primarily attributable to a relative or complete lack of insulin secretion by the beta cells of the pancreas or of defects of the insulin receptors, and a disease which is typically familial. Throughout the remainder of this specification and the claims, the term "diabetes" is intended to refer to diabetes mellitus.

Categories of diabetes specified by the National Institutes of Health include types I and II. Type I diabetes, formerly called juvenile-onset diabetes, includes patients who have abnormally low insulin levels and who are dependent upon insulin to prevent ketosis. If left untreated, ketosis can lead to ketoacidosis, coma, and death. Type II diabetes is non-insulin-dependent diabetes, and patients with this disease may have insulin levels which are normal or high, but decreased end organ sensitivity results in hyperglycemia. Neurological complications resulting from hyperglycemia can also progress to diabetic ketoacidosis, coma, and death. Other complications include peripheral neuropathy, mononeuritis multiplex, radiculopathy, autonomic neuropathy, cranial neuropathy, retinopathy, myelopathy, myopathy, nephropathy, teratogenicity, and premature atherosclerosis.

The goal of treatment of diabetes is to maintain insulin-glucose homeostasis, which may be controlled by diet alone in cases of mild early or late onset of the disease. In more severe cases, it is customary to administer a pharmacologic preparation of the insulin hormone to keep blood glucose levels below that where ketoacidosis is likely. Prescription insulin preparations vary in promptness, intensity, and duration of action, and may produce adverse reactions including hypoglycemia and insulin shock from excess dosage and hyperglycemia and diabetic ketoacidosis from inadequate dosage. Contraindications include possible adverse interaction with other drugs; increased insulin requirements in the presence of fever, stress and infection; allergic reactions to the insulin or components of the vehicle in which it is delivered; and decreased insulin requirements where liver or renal disease is present.

It is a principal object of the present invention to provide methods for treating diabetes by selectively increasing the secretion of insulin within the body whenever needed to maintain insulin-glucose homeostasis.

Normally, endogenous (naturally occurring) insulin hormone is secreted by the beta cells of islets in the pancreas in response to increased levels of glucose in the blood. As noted above, however, decreased end organ sensitivity can cause hyperglycemia even in individuals whose endogenous insulin levels are normal or even elevated. Moreover, blood glucose level is not the only stimulus for insulin secretion. The autonomic nervous system, through the vagus nerve, also affects insulin release (Rasmussen et al., Diabetic Care (1990) 13(6): 655-666). Daniel et al. reported in J. Physiol. (1967) 192: 317-327, finding a marked increase of pancreatic insulin release in baboons under vagal stimulation, but that hypoglycemia was not produced, possibly because of the low levels of stimulation.

A more specific object of the present invention is to apply techniques of selective modulation of the electrical activity of a cranial nerve of a patient, and particularly the vagus nerve, to increase or decrease the secretion of endogenous insulin, and thereby treat and control pancreatic disorders, particularly diabetes and hypoglycemia, respectively.

It is known that the nerves of the human body are generally composed of thousands of fibers of different sizes designated groups A B and C, which carry signals to and from the brain and other parts of the body. The vagus nerve, for example, may have approximately 100,000 fibers (axons) of the three different types, each of which carries such signals. Each axon of that nerve only conducts in one direction, in normal circumstances. The A and B fibers are myelinated (i.e., each has a myelin sheath composed largely of fat), whereas the C fibers are unmyelinated. Typically, myelinated fibers are larger, conduct electrical signals faster, and are electrically stimulated at much lower thresholds than unmyelinated fibers. Such fibers exhibit a particular strength-duration curve in response to a specific width and amplitude of stimulation pulse.

The A and B fibers are stimulated with relatively narrow pulse widths, from 50 to 200 microseconds ($\mu$s), for example. A fibers exhibit slightly faster electrical conductivities than the B fibers, and slightly lower electrical stimulation thresholds. The C fibers are relatively much smaller, conduct electrical signals very slowly, and have high stimulation thresholds typically requiring wider pulse widths (e g., 300-1000 μs) and higher amplitudes for activation. Although the A and B fibers may be selectively stimulated without also stimulating the C fibers, the magnitude and width of the pulse required for stimulating the C fibers would also activate A and B fibers.

Electrical stimulation of the nerve fiber typically activates neural signals in both directions (bidirectionally), but selective unidirectional stimulation is achievable through the use of special nerve electrodes and stimulating waveforms.

In a paper on the effects of vagal stimulation on experimentally induced seizures in rats (Eoilepsia (1990) 31 (Supp 2): S7-S19), Woodbury has noted that the vagus nerve is composed of somatic and visceral afferents (i.e., inward conducting nerve fibers which convey impulses toward a nerve center such as the brain or spinal cord) and efferents (i.e., outward conducting nerve fibers which convey impulses to an effector to stimulate it and produce activity). The vast majority of vagal nerve fibers are C fibers, and a majority are visceral afferents having cell bodies lying in masses or ganglia in the neck. The central projections terminate largely in the nucleus of the solitary tract which sends fibers to various regions of the brain (e.g, the hypothalamus, thalamus, and amygdala); others continue to the medial reticular formation of the medulla, the cerebellum, the nucleus cuneatus and other regions.

Woodbury further notes that stimulation of vagal nerve afferent fibers in animals evokes detectable changes of the EEG in all of these regions, and that the nature and extent of these EEG changes depends on the stimulation parameters. Chase, in *Exp Neurol* (1966) 16:36-49, had also observed that vagal activation can affect the EEG activity of certain parts of the brain. Woodbury also observes that vagal stimulation can produce widespread inhibitory effects on seizures and certain involuntary movements.

Extra-physiologic electrical stimulation of the vagus nerve has previously been proposed for treatment of epilepsy and various forms of involuntary movement disorders. Specifically, in U.S. Pat. 4,702,254 to J. Zabara (referred to herein as "the '254 patent"), a method and implantable device are disclosed for alleviating or preventing epileptic seizures, characterized by abnormal neural discharge patterns of the brain. The '254 patent describes an implantable neurocybernetic prosthesis (NCP) which utilizes neurocybernetic spectral discrimination by tuning the external current of the NCP generator to the electrochemical properties of a specific group of inhibitory nerves that affect the reticular system of the brain. These nerves are embedded within a bundle of other nerves, and are selectively activated directly or indirectly by the tuning of the NCP to augment states of brain neural discharge to control convulsions or seizures. According to the patent, the spectral discrimination analysis dictates that certain electrical parameters of the NCP pulse generator be selected based on the electrochemical properties of the nerves desired to be activated. The patent further indicates that the optimum sites for application of the NCP generator output to produce the desired effects are the cranial nerves in general, and the vagus nerve in particular.

The NCP disclosed in the '254 patent may be activated manually or automatically to provide treatment for the duration of the seizure. Manual activation is performed when the patient experiences the aura at onset of the seizure. Alternatively, automatic activation may be triggered upon detection of instantaneous changes in certain state parameters immediately preceding or at onset of a seizure. Additionally, a prophylactic or preventive mode may be employed in which the NCP is activated periodically to reduce the occurrence and/or the intensity of the seizures. The NCP stimulator of the '254 patent is implanted in the patient's chest and is connected to electrodes installed at the selected point of signal application at the nerve site with the more negative electrode situated closer to the brain and the positive electrode further from the brain, along the vagus nerve.

SUMMARY OF THE INVENTION

The present invention resides in methods and apparatus for treating systemic pancreatic disorders, and particularly diabetes (although they may also be useful for treating hypoglycemia), by selective vagal modulation. We hypothesize that vagal stimulation may be used to treat and control diabetes by stimulating pancreatic insulin release in patients whose pancreatic islets are capable of producing insulin. Nerves have trophic influences on tissues, and the vagal nerve stimulation can result in increased pancreatic insulin synthesis. It is further possible to reduce the quantity of insulin released in patients suffering from hypoglycemia, by inhibiting such release through inhibition of vagal activity.

The apparatus employed according to the invention comprises a neurostimulator for generating electrical pulses in a programmable pattern to produce the desired modulation of vagal electrical activity. According to a principal aspect of the invention, diabetes is treated by a stimulation strategy by which the electrical activity of the vagus nerve is modulated to increase the secretion of insulin by the pancreas. In the presently preferred embodiment, means are provided for patient activation of the neurostimulator at one or more prescribed times during the day, and/or the stimulation is programmed according to the circadian rhythm of the particular patient for activation shortly after meal periods.

Other techniques for triggering stimulation include the use of an external or implanted blood glucose sensor. It would be desirable for the neurostimulator which modulates the electrical activity of the vagus nerve to be activated by a sensor adapted to detect the blood glucose concentration level. One alternative is to take advantage of standard glucose test methods which are performed with an external (to the body) test device connected to a programmer to automatically adjust the stimulation parameters. Another alternative would be to incorporate an implanted sensor capable of such detection into the system. Unfortunately, long term glucose sensors are not currently available, although this has been an area of intense development effort in recent years. The present state of the art in glucose sensing and monitoring includes external devices for measuring glucose changes utilizing a subcutaneous sensor with a usable lifetime of only approximately two weeks, and a more recently developed infrared sensor which measures changes through a fingertip probe. The most prevalent technique currently in use for diabetic patients, however, is to prick the finger tip to draw blood for use in analysis of blood glucose concentration.

The present invention has the capability to interface with long term implanted sensors when they become available, and such an arrangement would then be preferred over either manual (patient) or circadian activation.

The neurostimulator is preferably but not necessarily implantable, and is arranged and adapted to selectively apply the desired therapy to treat the diabetes (or hypoglycemia, as the case may be) by modulating the electrical activity of the patient's vagus nerve in a predetermined manner. The device is initially programmed by the attending physician to provide the desired therapeutic modality for that purpose, and may be adapted as pointed out above for modification of the programming according to the results of the detection strategy.

Selection among various strategies for vagal modulation to treat diabetes depends on a number of factors. These include (i) a consideration of which of the nerve fibers are to be subjected to stimulation; (ii) the specific nature of the physiologic signal which is generated and techniques for its detection so that it ma be employed to trigger the modulation; and/or (iii) whether a "carry-over" or refractory period occurs after modulation in which the benefit of the modulation is maintained. Although these are not all of the factors to be considered for selecting a stimulation strategy, nor necessarily listed in order of importance, they are indicative of considerations which may apply in a specific case.

In the treatment according to the invention, different signal parameters and threshold curves are used to activate the various fibers of the patient's vagus nerve for selective modulation of the electrical activity thereof. By appropriately setting pulse width and amplitude of the electrical signal to be delivered by the neurostimulator to the patient's vagus nerve, the nerve fibers can be selectively stimulated, such as A and not B and C; or A and B, but not C; or A, B and C. Various related factors, however, must be considered in the selection process. For example, the C fibers conduct signals very slowly and are not highly responsive to techniques of fast stimulation because they become refractory after a relatively brief period of stimulation. Therefore, if it were desired to stimulate the C fibers in a particular patient, it would be prudent to use a short pulse train for the stimulus. Use of a long pulse train would be frustrated by the refractoriness of the fibers after a short interval of stimulation and their consequent incapability of tracking the pattern of the longer train. After a suitable recovery period, another short pulse train may be applied to achieve further treatment.

This phenomenon may also be exploited to inhibit C fiber activity. In this modality, high frequency pulses may be employed to "fatigue" the nerve and thereby inhibit its activity. In any case, the precise pattern to be used, e.g., the length of the time intervals on and off, will depend upon and be adjusted to the individual patient and whether diabetes or hypoglycemia is being treated.

The modulating signals applied to the vagus nerve may stimulate or inhibit neural signals to produce excitatory or inhibitory neurotransmitter release, but for purposes of this disclosure both situations are typically included within the term "stimulating". The vagus nerve is the preferred nerve site for application of the modulating signals, but it is possible that treatment of diabetes or hypoglycemia, albeit perhaps considerably less effective, could be achieved through application of the stimulus to one or more other nerves, and such treatment is deemed to be within the ambit of the present invention. The specific site at which the nerve electrode is implanted for vagal modulation may be in the neck or, alternatively, at or near the stomach, close to the pancreas.

Accordingly, it is another object of the present invention to apply the techniques of selective modulation of vagus nerve electrical activity, using a neurostimulator device which may be implantable, or disposed external to the body with only a small portion of the circuitry implanted or with only the nerve electrode(s) and associated lead(s) implanted percutaneously in the body, to the treatment and control of diabetes and other glucose abnormalities.

A more specific object of the invention is to provide methods and apparatus responsive to detected symptoms characteristic of or associated with diabetes and hypoglycemia for applying preprogrammed electrical stimuli to the vagus nerve of the patient to modulate the electrical activity of selected nerve fibers as part of a therapy designed to treat or control the diabetes and hypoglycemia.

BRIEF DESCRIPTION OF THE DRAWINGS

The above and still further objects, aspects, features and attendant advantages of the present invention will be better understood from a consideration of the ensuing detailed description of a presently preferred embodiment and method thereof, taken in conjunction with the accompanying drawings, in which.

DESCRIPTION OF THE PRESENTLY PREFERRED EMBODIMENTS AND METHODS

Figure 1:
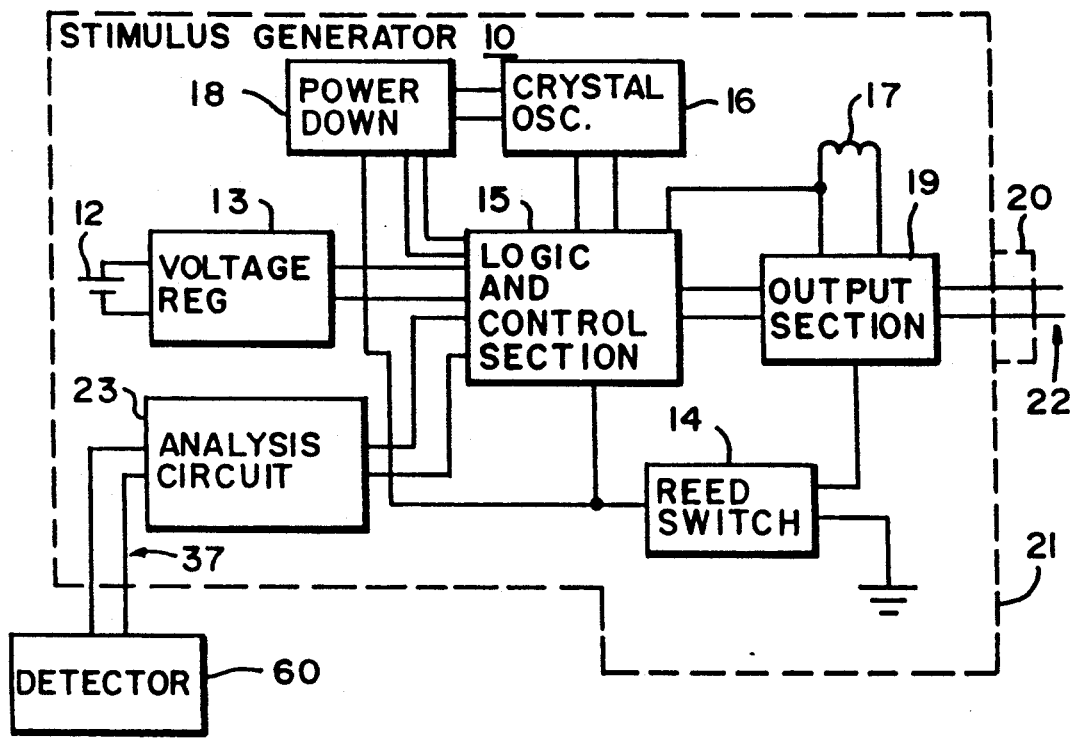
FIG. 1 is a simplified block diagram of an implantable neurostimulator (stimulus generator) for use (with appropriate parameter settings and ranges) in treating diabetes and hypoglycemia according to the present invention.
Figure 2:
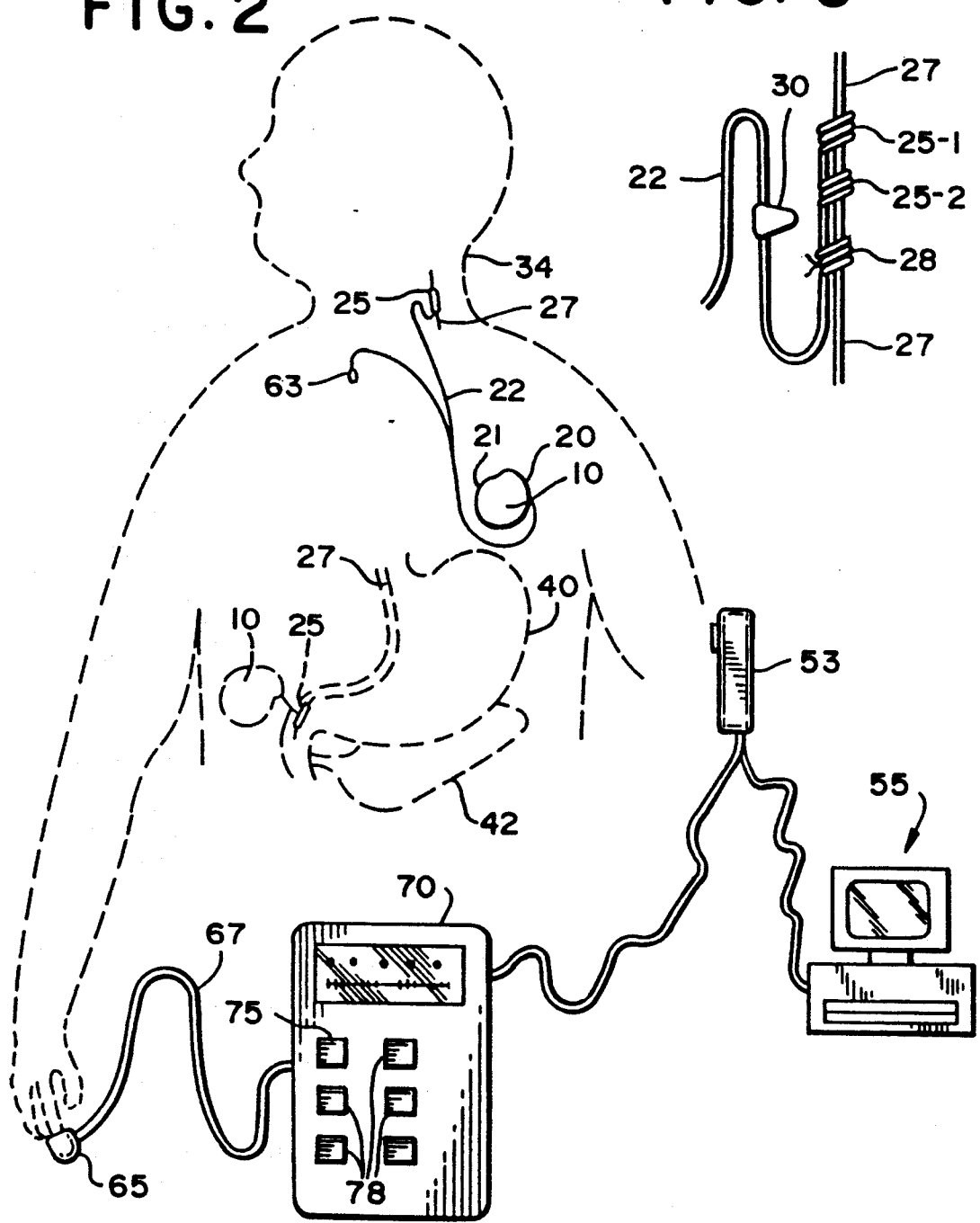
FIG. 2 is a simplified fragmentary illustration of two alternative locations of the stimulus generator and lead/electrode system of the neurostimulator implanted in the patient's body, and also illustrating the use of external or implanted sensing devices for determining blood glucose level, and a hand-held microprocessor analyzer/programmer for use with the neurostimulator.
Figure 3:
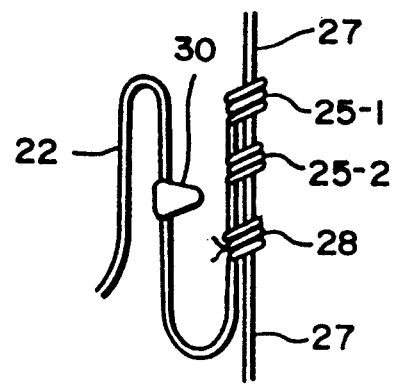
FIG. 3 is a detailed fragmentary illustration of the nerve electrode as implanted on the vagal nerve in the neck of the patient for modulating vagal activity.

Referring now to the drawings, a block diagram of the basic components of the stimulus generator of a neurostimulator and their interrelationship is illustrated in FIG. 1, and further details of location of an implantable version of the device and the associated lead/electrode system are shown in FIGS. 2 and 3. A generally suitable form of neurostimulator for use in the apparatus of the present invention is disclosed in copending U.S. patent application Ser. No 07/434,985, now U.S. Pat. No. 5,154,172 issued Oct. 13, 1992, in the names of Reese S. Terry, Jr., et al. (referred to herein as "the '172 patent), assigned to the same assignee as the instant application. The specification of the '172 patent is incorporated herein in its entirety by reference, but certain portions of it are summarized in this application for the sake of convenience to the reader.

The neurostimulator utilizes a conventional microprocessor and other standard electrical and electronic components, and in the case of an implanted device, communicates with a programmer and/or monitor located external to the patient's body by asynchronous serial communication for controlling or indicating states of the device. Passwords, handshakes and parity checks are employed for data integrity. The neurostimulator also includes means for conserving energy, which is important in any battery operated device and especially so where the device is implanted for medical treatment of a disorder, and means for providing various safety functions such as preventing accidental reset of the device.

The stimulus generator 10 (FIG. i) is preferably adapted to be implantable in the body of a patient 34, in a pocket formed by the surgeon just below the skin in the chest or, alternatively, below the skin at the abdominal cavity, as shown in FIG. 2. If desired, a primarily external neurostimulator may be employed instead. The neurostimulator also includes implantable stimulating electrodes (described below) together with a lead system 22 for applying the output signal of the stimulus generator to the patient's vagus nerve. Components external to the patient's body include a programming wand 53 for telemetry of parameter changes to the stimulus generator and monitoring signals from the generator, and a computer 55 and associated software for adjustment of parameters and control of communication between the generator, the programming wand and the computer (see FIG. 2).

In conjunction with its microprocessor-based logic and control circuitry, the stimulus generator 10 may include or be used in conjunction with a detector for use, together with an analysis circuit or system 23, in determining the blood glucose level of the patient on a continual or a periodic basis. The detector may be in the form of an implantable long term blood glucose concentration monitor 60 (although not currently available, such a device would be usable with the present invention) in which the sensor portion 63 (FIG. 2) may be disposed within a blood vessel on an intravenous lead or catheter connected to analyzer system of the stimulus generator. The extent, if any, to which insulin secretion by the pancreas should be increased or inhibited is determined from such analysis, and the appropriate response is implemented by triggering automatic delivery of a modulating signal to the patient's vagus nerve.

For present purposes, until such implantable or partially implanted detection systems are fully perfected and simplified, and/or to eliminate the cost of detection systems and the surgical procedures required to implant them, it is preferable to provide for manual activation of the neurostimulator by the patient after simple determination of blood glucose concentration by conventional procedures such as drawing and analyzing a blood sample. Alternatively, the patient may use an infrared sensor of the type recently developed in which glucose concentration changes are measured using a finger tip probe or cuff 65 (FIG. 2). In the latter case, the patient 34 places the cuff 65 on the finger tip, manually activates the photic device (not shown) therein, and the sense signal therefrom is applied via an electrical lead 67 to a microprocessor based hand-held analyzer/programmer 70 for determining blood glucose concentration. The size of the analyzer/programmer 70 is intentionally exaggerated relative to the other portions of FIG. 2, to clearly display certain functions of that device, as will be described presently. Based on the results of the analysis, the patient is informed of the need to activate the neurostimulator to stimulate secretion of insulin by the pancreas.

Another alternative is to activate the neurostimulator manually by patient initiation or automatically by circadian programming at appropriate times of the day corresponding to (e.g., following) mealtimes. In either of the latter cases, the programming may be set by the physician so that the patient may select or the automatic selection is made based on breakfast, lunch, dinner or snack typical consumption and related increase in glucose level. For manual activation, the patient may depress a program key 75 and then one of the other keys 78 on the hand-held programmer 70 which are appropriately labeled for the type and extent of food to be consumed. While operating the programmer, the wand 53 is placed adjacent to the implanted generator 10.

The stimulus generator is designed, implemented and preprogrammed so that in each such instance it delivers a selectively patterned stimulating signal to modulate the electrical activity of the vagus nerve to stimulate secretion of the proper amount of insulin by the pancreas, and thereby treat and control the diabetes. For the patient suffering from hypoglycemia, the control signal for application to the vagus nerve is preset and selected to inhibit the secretion of insulin by inhibiting vagal activity.

As shown in FIG. 1, stimulus generator 10 includes a battery (or set of batteries) 12, which may be of any reliable long-lasting type conventionally employed for powering implantable medical electronic devices (such as batteries employed in implantable cardiac pacemakers or defibrillators). In the presently preferred embodiment of the stimulus generator, the battery is a single lithium thionyl chloride cell. The terminals of the cell 12 are connected to the input side of a voltage regulator 13. The regulator smoothes the battery output to produce a clean, steady output voltage, and provides enhancement thereof such as voltage multiplication or division if necessary for a specific application.

Regulator 13 supplies power to logic and control section 15, which includes a microprocessor and controls the programmable functions of the device. Among these programmable functions are output current or voltage, output signal frequency, output signal pulse width, output signal on-time, output signal off-time, daily treatment time for continuous or periodic modulation of vagal activity, and output signal-start delay time. Such programmability allows the output signal to be selectively crafted for application to the stimulating electrode set 25 (FIGS. 2 and 3) to obtain the desired modulation of vagal activity for the treatment regimen. Timing signals for the logic and control functions of the generator are provided by a crystal oscillator 16. A magnetically-actuated reed switch 14 is incorporated in the electronics package to provide the generator with the capability for patient activation thereof by selective placement of an external magnet immediately adjacent to the package or its implant site.

Built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

A power down circuit 18 may be electrically connected to reed switch 14 and logic/control circuit 15 and timed by the clock pulses from the crystal oscillator 16 to reduce power to the microprocessor of section 15 and/or to the oscillator to a point at which the device is essentially in a sleep state but sufficiently alert to be awakened on command. The power down mode or sleep state may be initiated automatically within, say, two hours after the device has been activated to generate its programmed stimulating output signal, and may remain in that mode for two to five hours. These time intervals may be longer or shorter depending on the needs of the particular patient. Alternatively, the device may stay in a reduced power state until the power down circuit is disabled to wake the microprocessor by manual activation of the device by the patient. Power down circuits fabricated in CMOS semiconductor circuitry are well known in the integrated circuit field, and such a circuit is readily incorporated in the neurostimulator device.

The reduced power requirement of the device in the interval assures the availability of sufficient battery power to enable treatment over a much longer battery lifetime than would otherwise be the case. As a result, the time interval between required surgical replacements of the device may be substantially increased, and the device size may be considerably shrunken owing to a reduced battery size.

Logic and control section 15 of the stimulus generator controls an output circuit or section 19 which generates the proper programmed signal levels. The programmed output signal of section 15 is fed, via an electrical connector 20 on the generator case (housing) 21, to the lead assembly 22 which is connected at its distal end to the stimulating electrodes (FIGS. 2 and 3). As noted earlier herein, analyzer circuit 23 may be provided within the generator housing 21, with connections to the microprocessor in logic and control section 15 and to sensing electrodes connected to an implanted glucose concentration detector 60.

Preferably, however, the device is programmed to cause secretion of insulin by the pancreas (in patients whose pancreatic islets are capable of producing insulin, which constitutes the great majority of diabetic patients) upon device activation by the patient following direct measurement of blood glucose by drawing and analyzing a blood sample (not shown) in the usual manner, or by use of an external fingertip cuff infrared sensor 65 and associated glucose concentration microprocessor-based analyzer 70 in the manner described above. An alternative is to selectively activate the device to stimulate the vagus nerve at a preselected time or times in each circadian cycle (or in each 24-hour day), such as within a few minutes to an hour following the patient's customary mealtimes. Automatic activation may be provided by a timer controlled by crystal oscillator 16. Manual activation by the patient, in response to direct measurements of blood glucose or to symptoms, may be accomplished in the manner described above using programmer 70 and wand 53.

The parameters of the stimulating signal of the implanted device may be calibrated by telemetry (via the programming wand) according to the needs of the particular patient, and programmed into the microprocessor for delivery of treatment by activation of the stimulus generator according to the prescribed regimen. The stimulus generator may be programmed, for example, with an IBM-compatible personal computer 55 using programming software of the type copyrighted by the assignee of the instant application with the Register of Copyrights, Library of Congress, or other suitable software based on the description herein, and programming wand 53. The wand and software permit noninvasive communication with the generator after the latter is implanted. The wand is preferably powered by internal batteries, and provided with a "power on" light to indicate sufficient power for communication. Another indicator light is preferably provided to show that data transmission is occurring between the wand and the generator.

Housing 21 in which stimulus generator 10 is encased is hermetically sealed and composed of a suitable conventional material such as titanium which is biologically compatible with the fluids and tissue of the patient's body. Further details of structure and operation of the neurostimulator, beyond those by which the device is adapted to treat the disorder described herein, are available in the '895 application, to which the reader is referred.

FIG. 2 illustrates alternative locations of generator 10, in case 21 with connector 20, for an implanted system. In either case, the generator is implanted in the patient's chest in a pocket formed by the surgeon just below the skin. One suitable location for the generator is in the patient's chest, as a pacemaker pulse generator would be implanted, with the nerve electrode array 25 and associated lead 22 implanted in the patient's neck. The stimulating nerve electrode set 25 (FIG. 3) is conductively connected to the distal end of insulated electrically conductive lead assembly 22 which is attached at its proximal end to connector 20. Electrode set 25 is a bipolar stimulating electrode, preferably of the type described in U.S. Pat. No. 4,573,481 issued Mar. 4, 1986 to Bullara. The electrode assembly in this particular instance is surgically implanted on the vagus nerve 27 in the patient's neck. The two electrodes 25-1 and 25-2 are wrapped about the vagus nerve, and the assembly is secured to the nerve by a spiral anchoring tether 28 preferably as disclosed in U.S. Pat. No. 4,979,511 issued Dec. 25, 1990 to Reese S. Terry, Jr. and assigned to the same assignee as the instant application. Lead(s) 22 is secured, while retaining the ability to flex with movement of the chest and neck, by a suture connection 30 to nearby tissue.

The open helical design of electrode assembly 25 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum constituting the electrodes which are individually bonded to the inside surface of each of the first two spiral loops 25-1 and 25-2 of a three-loop helical assembly, and the two lead wires are respectively welded to the conductive ribbon electrodes. The remainder of each loop is composed of silicone rubber, and the third loop acts as the tether 28 for the electrode assembly. The inner diameter of the helical bipolar electrode assembly may typically be approximately two millimeters (mm), and an individual spiral is about seven mm long (measured along the axis of the nerve).

Instead of implanting the nerve electrode assembly in the patient's neck, the assembly may be implanted on the vagus nerve on the stomach 40 closer to the pancreas 42, to enhance sensitivity to the modulation of vagal activity. The implantation of electrode set 25 is accomplished in substantially the same manner as was described for the neck location. Here, however, the stimulus generator 10 is implanted along the abdominal cavity.

If an implantable blood glucose concentration sensor were available, the system may be arranged and adapted using the implanted detector such as 60 in conjunction with internal analysis circuit 23 to perform a comparison with a calibrated threshold level, to initiate insulin secretion in incremental amounts by stimulating the vagus nerve with the designed signal in brief or progressively shorter intervals of time until an excessive blood glucose level has returned to normal (the predetermined threshold level. For hypoglycemia, the treatment would again be implemented to inhibit the vagal activity to suppress insulin secretion.

Figure 4:
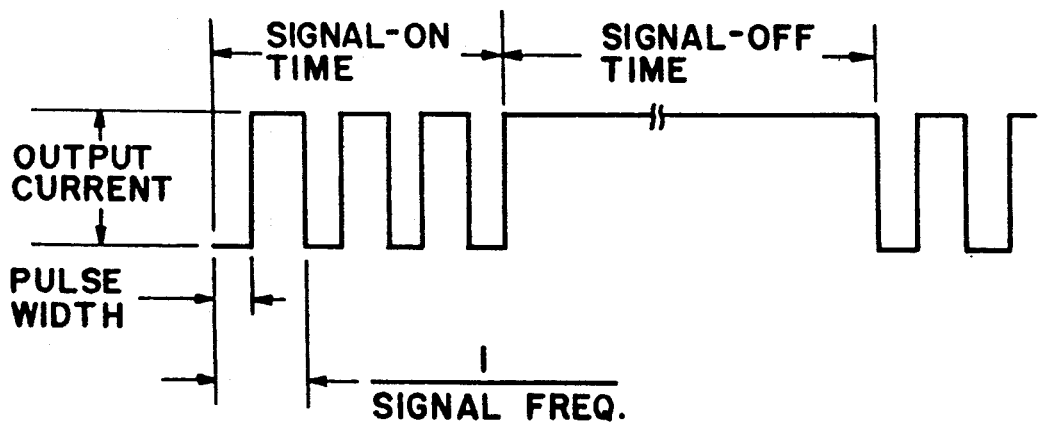
FIG. 4 is an illustrative idealized electrical output signal waveform of the stimulus generator useful for clarifying relevant parameters of the signal developed by the stimulus generator for application to the nerve.

The operation of stimulus generator 10 to control and treat diabetes and hypoglycemia will be described by reference to the signal waveform and parameters shown in FIG. 4. The latter is an idealized representation of the output signal delivered by output section 19 of the neurostimulator to electrode assembly 25. This illustration is presented principally to clarify terminology, including the parameters of output signal on-time, output signal off-time, output signal frequency, output signal pulse width, and output signal current or voltage. A suitable range of stimulation parameters and the typical value of each parameter of the stimulating output signal for treatment of diabetes are set forth in Table I below:

TABLE I

|  | Range | Typical |
|---|---|---|
| Pulse Width | 0.05–1.5 ms* | 0.1 ms |
| Output Current | 0.1–5.0 mA** | 1.0 mA |
| Frequency | 5–150 Hz*** | 12 Hz |
| ON Time | 500–10,000 sec | 6,000 sec |
| OFF Time | 500–10,000 sec | 6,000 sec |
| Frequency sweep | 10–50 Hz | Optional |
| Random frequency | 10–50 Hz | Optional |

[*milliseconds; milliamperes; *Hertz (cycles per second)]

A suitable range of parameters and the typical value of each parameter of a stimulating (inhibiting) signal to be applied to the vagus nerve for treatment of hypoglycemia are set forth in Table II below:

TABLE II

|  | Range | Typical |
|---|---|---|
| Pulse Width | 0.05–1.5 ms | 0.5 ms |
| Output Current | 0.1–5.0 mA | 1.5 mA |
| Frequency | 5–150 Hz | 100 Hz |
| ON Time | 5–5000 sec | 500 sec |
| OFF Time | 5–5000 sec | 10 sec |
| Frequency sweep | 10–50 Hz | Optional |
| Random frequency | 10–50 Hz | Optional |

Various features may be incorporated into the neurostimulator for purposes of the safety and comfort of the patient. For example, comfort is enhanced by programming the output stimulus to ramp up during the first two seconds of stimulation, rather than to be delivered abruptly. Also, the implanted generator may be provided with a clamping circuit to limit the maximum voltage delivered to the vagus nerve (for example, to 14 volts). The maximum limit is set to prevent injury or trauma to the patient's vagus nerve.

The programmable functions and capabilities of the neurostimulator are designed and implemented to permit noninvasive communication with the stimulus generator after it is implanted, which is useful for both activation and monitoring functions. Beyond the essential functions of the device, the programming software may readily be structured to provide straightforward menu-driven operation, HELP functions, prompts, and message to facilitate simple and rapid programming while keeping the user fully informed of everything occurring at each step of a sequence. Programming capabilities should include capability to modify the adjustable parameters of the stimulus generator and its output signal, to test device diagnostics, and to store and retrieve telemetered data. It is desirable that when the implanted unit is interrogated, the present state of the adjustable parameters is displayed on the monitor of external PC so that the programmer may then conveniently change any or all of those parameters at the same time; and, if a particular parameter is selected for change, all permissible values for that parameter are displayed so that the programmer (typically, limited to the attending physician) may select an appropriate desired value for entry into the neurostimulator.

Diagnostics testing may be used to verify proper operation of the device, and to indicate the existence of problems such as with communication, the battery, or the lead/electrode impedance. A low battery reading, for example, would be indicative of imminent end of life of the battery and need for implantation of a new device. The nerve electrodes are capable of indefinite use absent indication of a problem with them observed on the diagnostics testing.

Although a preferred embodiment and method of controlling endocrine disorders have been described herein, it will be apparent to those skilled in the field from a consideration of the foregoing description that variations and modifications may be made without departing from the spirit and scope of the invention. For example, a totally implantable neurostimulator device need not be utilized. Instead, the electronic energization package may be primarily external to the body, and stimulation achieved with an RF power device implemented to provide the necessary energy level. The implanted components may be limited to the lead/electrode assembly, a coil and a DC rectifier, and pulses programmed with the desired parameters transmitted through the skin with an RF carrier. The signal is rectified to regenerate a pulsed signal for application as the stimulus to the vagus nerve to modulate vagal activity. This virtually eliminates battery changes, but has the disadvantages that the external transmitter must be carried by the patient, greater power is required for activation, and the output current to the nerve is less stable.

An external stimulus generator may be employed with leads extending percutaneously to the implanted nerve electrode set. The major problem here is the potential for infection, but such temporary arrangement is useful to allow short term testing to determine whether a particular patient's endocrine disorder may be successfully controlled and treated with the neurostimulator. If the results are conclusive or promising, a more permanent implant may be provided.

Accordingly, it is intended that the invention shall be limited only to the extent required by the appended claims and the rules and principles of applicable law.

What is claimed is:

1. A method of treating pancreatic endocrine disorders in patients, which includes the steps of:

detecting a blood glucose concentration indicative of an endocrine disorder in the patient, and in response to such detection, selectively applying a predetermined electrical signal to the patient's vagus nerve for modulation of electrical activity thereof to adjust secretion of endogenous insulin and thereby control the endocrine disorder.

2. The method of claim 1, including:

applying a pulse waveform with programmable signal parameters as the predetermined electrical signal.

3. The method of claim 1, wherein: the step of applying the electrical signal is performed by manual initiation by the patient.

4. The method of claim 1, including:

programming the electrical signal to occur at one or more predetermined times during the patient's circadian cycle.

5. The method of claim 1, wherein:

the step of detecting blood glucose concentration is performed external to the patient.

6. The method of claim 1, wherein the endocrine disorder is diabetes mellitus, and including:

programming the electrical signal for application to stimulate vagal activity to increase the secretion of endogenous insulin.

7. The method of claim 1, wherein the endocrine disorder is hypoglycemia, and including:

programming the electrical signal for application to inhibit vagal activity to suppress the secretion of endogenous insulin.

8. The method of claim 1, including:

programming the electrical signal to modulate vagal activity to an extent according to the type and amount of food consumed by the patient.

9. The method of claim 8, wherein:

the step of applying the electrical signal is performed by manual activation by the patient.

10. The method of claim 1, wherein:

the step of applying the electrical signal includes implanting an electrode on the vagus nerve in the neck of the patient.

11. The method of claim 1, wherein:

the step of applying the electrical signal includes implanting an electrode on the vagus nerve at the stomach of the patient.

12. In a method for treatment and control of diabetes in a patient, the steps of:

providing a programmable device responsive, when activated, to apply a programmed electrical signal to the patient's vagus nerve for stimulation thereof to adjust secretion of endogenous insulin appropriate to maintain insulin-glucose homeostasis in the patient's bloodstream and thereby control the diabetes, and periodically activating the device to maintain the homeostasis.

13. The method of claim 12, wherein:

the step of periodically activating is implemented manually by the patient.

14. The method of claim 12, wherein:

the step of periodically activating is implemented by programming the device to apply the signal according to circadian rhythm of the patient.

15. The method of claim 12, wherein:

the step of providing the device includes implementing the device to generate said electrical signal in the form of a pulse waveform with programmable signal parameters including at least some of pulse width, output current or voltage, frequency, on time and off time.

16. Apparatus for treating pancreatic endocrine disorders in human patients, comprising, in combination:

stimulus means responsive, when activated, to generate a programmable electrical waveform, electrode means electrically connectable to said stimulus means and adapted to be implanted for delivering said waveform to a nerve of the patient preselected according to its capability to affect the secretion of natural insulin by the patient's pancreas, programming means for programming said waveform with parameter values selected, when the electrode means and the stimulus means are electrically connected and the stimulus means is activated, to modulate electrical activity of said nerve to adjust secretion of natural insulin for controlling the endocrine disorder, and activation mans for selectively activating said stimulus means, including sensing means adapted for detecting a blood glucose level of the patient indicative of a need to adjust insulin secretion.

17. The apparatus of claim 16, wherein the activation means further includes:

triggering means for activating the stimulus means in response to detection of said blood glucose level by the sensing means.

18. The apparatus of claim 16 wherein:

said sensing means is adapted to be carried on the body of the patient.

19. The apparatus of claim 16, wherein:

said stimulus means is adapted for implantation into the body of the patient.

20. The apparatus of claim 19, wherein:

said stimulus means includes a battery, and means for powering down the stimulus means a predetermined time interval after activation thereof to conserve consumption of energy from the battery, said time interval being predetermined to allow sufficient time for adjustment of insulin secretion to control the endocrine disorder.

21. The apparatus of claim 16, wherein the activation means further includes:

manual activating means for patient selection of a plurality of different levels of electrical stimulation of the vagus nerve to vary the secretion of insulin according to the nature and amount of food consumed by the patient.

22. The apparatus of claim 16, wherein:

the sensing means includes means adapted for detecting the blood glucose level at a finger tip of the patient.

* * * * *